United States Patent
Schmidt

(10) Patent No.: US 10,028,709 B2
(45) Date of Patent: Jul. 24, 2018

(54) ARRANGEMENT WITH A COLLISION DETECTION DEVICE, MEDICAL IMAGING APPARATUS WITH A COLLISION DETECTION DEVICE, AND METHOD FOR OPERATING A COLLISION DETECTION DEVICE

(71) Applicant: Verena Schmidt, Erbendorf (DE)

(72) Inventor: Verena Schmidt, Erbendorf (DE)

(73) Assignee: Siemens Aktiengesellschaft, München (DE)

( * ) Notice: Subject to any disclaimer, the term of this patent is extended or adjusted under 35 U.S.C. 154(b) by 98 days.

(21) Appl. No.: 14/952,976

(22) Filed: Nov. 26, 2015

(65) Prior Publication Data
US 2016/0143600 A1    May 26, 2016

(30) Foreign Application Priority Data
Nov. 26, 2014  (DE) .................. 10 2014 224 171

(51) Int. Cl.
*A61B 6/10* (2006.01)
*A61B 6/00* (2006.01)

(52) U.S. Cl.
CPC ............ *A61B 6/102* (2013.01); *A61B 6/4441* (2013.01)

(58) Field of Classification Search
CPC ..... H04W 4/008; H04W 4/003; H04W 4/046; H04W 4/005; H04W 4/027; H04W 84/005; H04W 84/12; H04W 4/001; G07C 5/008; G07C 5/006; G07C 5/02; G07C 2009/00769; G07C 5/0808; H04L 67/12; H04L 2012/402
See application file for complete search history.

(56) References Cited

U.S. PATENT DOCUMENTS

| 5,570,770 A | 11/1996 | Baaten et al. |
| 5,878,112 A * | 3/1999 | Koertge ............... F16P 3/12 |
| | | 378/209 |

(Continued)

FOREIGN PATENT DOCUMENTS

| CN | 1486673 A | 4/2004 |
| CN | 1969752 A | 5/2007 |

(Continued)

OTHER PUBLICATIONS

German Office action for related German Application No. 10 2014 224 171.5, dated Aug. 14, 2015, with English Translation.

(Continued)

*Primary Examiner* — Hoon Song
(74) *Attorney, Agent, or Firm* — Lempia Summerfield Katz LLC

(57) ABSTRACT

An arrangement with a movable apparatus part is provided. The arrangement includes a mat-like, removable collision detection device arranged on the apparatus part and a plurality of first fasteners of the collision detection device. The plurality of first fasteners are configured to form a releasable connection with corresponding second fasteners of the apparatus part. The arrangement also includes an electrical monitoring unit configured to monitor an electrical resistance of the connection of the plurality of first fasteners to the second fasteners. A medical imaging apparatus with such an arrangement, and an associated method are also provided.

17 Claims, 2 Drawing Sheets

(56) References Cited

U.S. PATENT DOCUMENTS

| | | |
|---|---|---|
| 8,653,837 B2 | 2/2014 | Frangen |
| 2004/0042587 A1 | 3/2004 | Deshpande |
| 2007/0164574 A1* | 7/2007 | Tanabe .................. B60R 19/483 293/102 |
| 2008/0089483 A1 | 4/2008 | Nivestedt et al. |
| 2011/0050256 A1 | 3/2011 | Frangen |
| 2011/0282164 A1 | 11/2011 | Yang et al. |
| 2013/0271147 A1 | 10/2013 | Ostermoller |
| 2014/0130810 A1 | 5/2014 | Azizian et al. |
| 2016/0097689 A1* | 4/2016 | Su ........................ A61B 5/1036 73/862.046 |

FOREIGN PATENT DOCUMENTS

| | | |
|---|---|---|
| CN | 101022851 A | 8/2007 |
| CN | 102003612 A | 4/2011 |
| DE | 102009029021A1 A1 | 3/2011 |
| EP | 2441385A1 A1 | 4/2012 |
| WO | 2010083630 A1 | 7/2010 |

OTHER PUBLICATIONS

Chinese Office Action for Chinese Application No. 201510834508.6, dated Feb. 2, 2018.

* cited by examiner

ARRANGEMENT WITH A COLLISION DETECTION DEVICE, MEDICAL IMAGING APPARATUS WITH A COLLISION DETECTION DEVICE, AND METHOD FOR OPERATING A COLLISION DETECTION DEVICE

This application claims the benefit of DE 10 2014 224 171.5, filed on Nov. 26, 2014, which is hereby incorporated by reference in its entirety.

FIELD

The present embodiments relate to an arrangement with a movable apparatus part or a housing of the apparatus part, on which a collision detection device is arranged, a medical imaging apparatus with such an arrangement, and an associated method for operating the collision detection device.

BACKGROUND

Collision detection devices in moved machines, apparatuses, or robots may be integrated in a housing cover. Housing covers for collision detection are also used in medical imaging apparatuses. A medical imaging apparatus with collision detection is known from the U.S. Pat. No. 5,570,770, for example.

Medical imaging apparatuses for medical diagnosis or therapy generally have an X-ray emitter and an X-ray detector. Each of the X-ray emitter and the X-ray detector is in a housing. These two components are arranged at a distance from each other. A patient to be examined or to be treated is positioned between the X-ray emitter and the X-ray detector. The X-ray emitter and the X-ray detector are positioned relative to the body of the patient such that an image of the desired cross section of the interior of the body may be taken. The medical apparatus may in most cases be oriented and positioned with the aid of a motorized drive.

Apparatuses of this kind are often equipped with a C-arm (e.g., an arc-shaped mount that may be rotated about several planes with the aid of a rail system). During the use of the medical imaging apparatus, a moved part (e.g., the X-ray detector) comes close to the object to be examined in order to achieve the desired image quality. The X-ray detector has a comparatively large front face for receiving the X-rays, and any desired point on this front face or on the periphery may come into contact with the patient to be examined. Such a collision may occur in any direction of movement of the X-ray detector. This is undesirable, and therefore, an apparatus of this kind is equipped with a detection device for detecting the collision with an object.

If a contact between the movable part of the apparatus and the object is detected, the movement of the apparatus may be stopped in order to minimize the severity of the consequences of a collision. In the U.S. Pat. No. 5,570,770, a medical X-ray apparatus that is equipped with an electrical detection device for detecting collisions is described. Sensors in the apparatus are configured to measure the current and the power consumed by the drive motor. These parameters give an indication of the instantaneous force exerted on the movable part. This instantaneous value may be compared with an expected value for the force. If the difference between the instantaneous value and the expected value exceeds a predetermined threshold value, it is assumed that the movement of the movable part is impeded by an object and a collision is thus taking place. Accordingly, an alarm signal is generated, and the movement is stopped.

Housing covers for movable medical imaging apparatuses or parts of covers, in which a collision with an object acts on an electric switch or on electrically switchable contacts, are known. Housing covers of these kinds are, for example, mounted on springs, of which the positional shift caused by a collision is detected. There are solutions with elastic materials that, with a predeterminable resilience, activate the electric switch. The switching signals thus obtained are used to switch off a movement of the medical imaging apparatus.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an arrangement with a collision detection device, a medical imaging apparatus with a collision detection device, and an associated method for operating a collision detection device are provided.

According to one or more of the present embodiments, the arrangement includes a movable apparatus part (e.g., a C-arm of an X-ray apparatus), on which a mat-like collision detection device is arranged. Alternatively, the mat-like collision detection device may also be arranged on a housing of the apparatus part. The correct mounting of the collision detection device is monitored electrically. This purpose is served by first fastening elements of the device. The first fastening elements may form a releasable connection with corresponding second fastening elements of the apparatus part or of the housing. The correct connection (e.g., closed fastening elements) is monitored, and in the case of an open connection, an error signal or a warning signal may be emitted or the open connection may be indicated optically or acoustically.

In one embodiment, an arrangement with a movable apparatus part is provided. A mat-like collision detection device is arranged removably on the apparatus part. The arrangement includes a plurality of first fastening elements of the collision detection device. The first fastening elements are configured to form a releasable connection with corresponding second fastening elements of the apparatus part. The arrangement further includes an electrical monitoring unit that is designed and programmed to electrically monitor the electrical resistance of the connection of the first to the second fastening elements. Instead of being arranged on the apparatus part itself, the collision detection device may also be arranged on a housing of the apparatus part.

One or more of the present embodiments afford the advantage of allowing a collision detection device to be mounted without using tools. In this way, the collision detection device may be easily installed and uninstalled. Even the operating personnel may carry this out for disinfection, for example. A correct re-installation is provided by the electrical monitoring of the resistance of the connection. Inadvertent release of the collision detection device may likewise be detected.

In one development, the first and second fastening elements are electrically conductive.

In a further embodiment, the first and the second fastening elements are configured as press studs or hook-and-loop fasteners.

In a further embodiment, the arrangement includes an output unit that is designed and programmed to optically and/or acoustically indicate the state of the connections between corresponding first and second fastening elements.

The display unit may be configured to emit a warning signal and/or to stop a movement of the apparatus part if the monitoring unit detects an open connection between one of the corresponding first and second fastening elements.

In a further embodiment, the monitoring unit may be designed and programmed to determine an electrical resistance between adjacent second fastening elements. Adjacent corresponding first fastening elements are electrically short-circuited to each other.

A medical imaging apparatus (e.g., an X-ray apparatus) includes one embodiment of the arrangement.

In one embodiment, a method for operating a mat-like collision detection device arranged removably on a moved apparatus part or on a housing of the apparatus part is provided. The electrical resistance of a connection of first fastening elements of the collision detection device to corresponding second fastening elements of the apparatus part or of the housing is electrically monitored.

In a development of the method, the electrical resistance between adjacent second fastening elements may be determined. The first and second fastening elements are electrically conductive, and corresponding adjacent first fastening elements are short-circuited.

DETAILED DESCRIPTION

Figure 1:
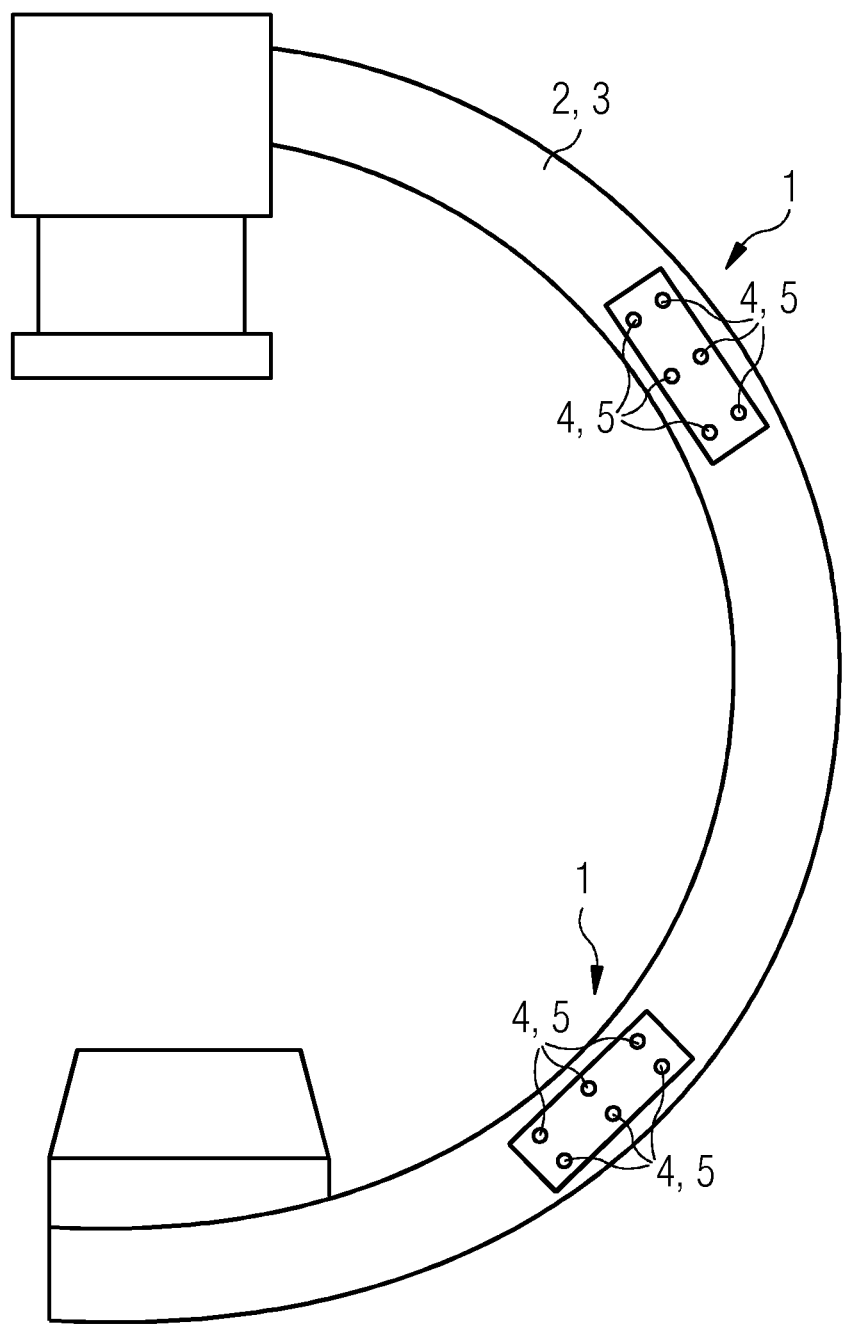
FIG. 1 shows a side view of one embodiment of a collision detection device on a C-arm of an X-ray apparatus.

FIG. 1 shows one embodiment of a medical imaging apparatus. The subject matter of the present embodiments may be used analogously on any machine with moved apparatus parts.

FIG. 1 shows a movable apparatus part 2 with a housing 3 of one embodiment of a medical imaging apparatus. A C-arm of an X-ray apparatus is shown by way of example. Two collision detection devices 1 are mounted on a housing 3. The collision detection devices 1 may detect contacts or collisions with an object and cause a movement of the apparatus part 2. At the same time, the collision detection devices 1 may also serve as collision protection.

The collision detection device 1 is configured as a mat and includes sensors for the collision detection. The collision detection device is not connected fixedly to the housing 3 and instead may be removed when necessary. For this purpose, the collision detection device 1 includes first fastening elements 4 (e.g., fasteners) that are connected releasably to corresponding second fastening elements 5 (e.g., fasteners) of the housing 3. As a result of these closed connections, the collision detection device 1 sits fixedly on the housing 3. The first and second fastening elements 4, 5 may be configured as press studs, for example.

A press stud is a closure including two small, round parts, of which one is provided with a recess and the other is provided with a matching head. The two small, round parts are pressed one into the other until closed. To provide that the head snaps into place and that the stud opens only under a considerable pulling force, the recess is suitably shaped as an open cavity or ring. The material elasticity of the stud thus permits a snap fit, or an additional laterally deflecting element is fitted. Press studs are in most cases made of metal. Alternatively and less commonly, the press studs are made of plastic.

To provide that the collision detection device 1 is actually fixedly connected to the housing 3, the connections of the first to the second fastening elements 4, 5 are electrically monitored. This is shown more closely in FIG. 2.

As an alternative to press studs, hook-and-loop fasteners may also be used. Correct connections of the hook-and-loop fasteners are monitored or have additional monitoring points.

Figure 2:
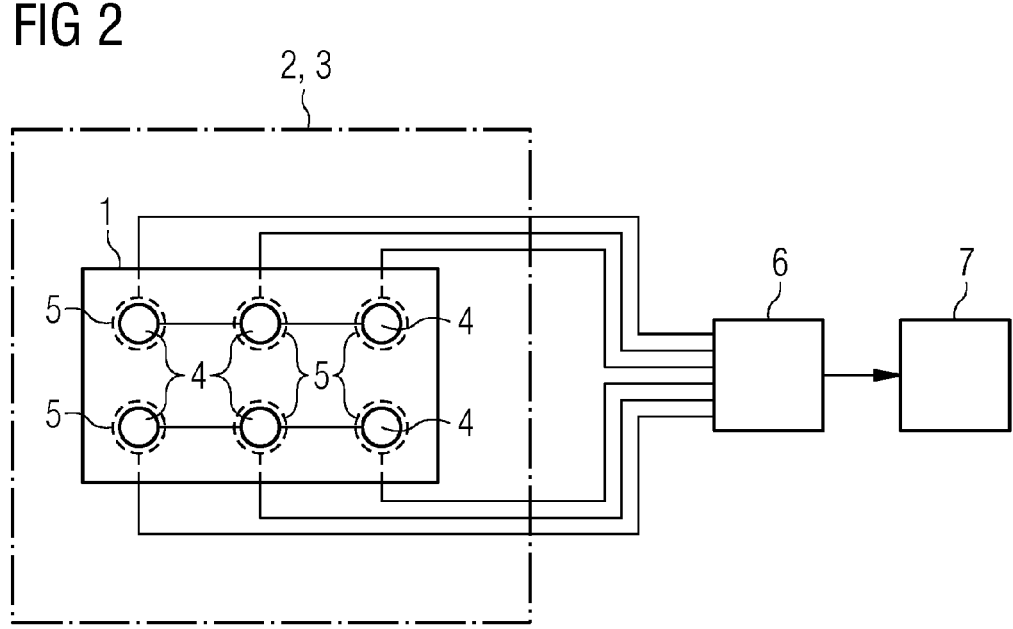
FIG. 2 shows a block diagram of one embodiment of an arrangement with a collision detection device.

FIG. 2 shows a block diagram with an exemplary apparatus part 2 or with an exemplary housing 3. Second fastening elements 5 (e.g., lower parts of press studs) are arranged at a distance from one another on the apparatus part 2. Corresponding to these, first fastening elements 4 (e.g., the upper parts of the press studs) are arranged on the collision detection device 1 and may form a releasable connection with the second fastening elements 5. The first and second fastening elements 4, 5 are electrically conductive and, for example, made of metal.

Each second fastening element 5 is electrically connected to the monitoring unit 6. Adjacent first fastening elements 4 are short-circuited to one another (e.g., by a wire connection). The monitoring unit 6 measures the electrical resistance between two adjacent second fastening elements 5. If the resistance is almost equal to zero (e.g., short circuit), the connection is correctly closed. In this way, each individual connection point may be monitored since the electrical resistance of each connection is measured.

The monitoring unit 6 is connected to an output unit 7 with which an error message may be emitted acoustically or optically to indicate an open or incorrectly closed connection. Alternatively or in addition, the connection state for each connection point may be shown in graph form, or the movement of the apparatus part 2 may be stopped.

Although the invention has been illustrated and described in detail based on the illustrative embodiments, the invention is not limited by the disclosed examples. Other variations may be derived from these by a person skilled in the art without departing from the scope of the invention. For example, the invention may also be used in non-medical applications (e.g., in robots).

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An arrangement of a medical imaging device with a movable apparatus part, the arrangement comprising:
    a mat-like, removable collision detection device arranged on the movable apparatus part of the medical imaging device;

a plurality of first fasteners arranged on the collision detection device, the plurality of first fasteners being configured to form a releasable connection with corresponding second fasteners, the second fasteners being arranged on the movable apparatus part, the collision detection device being connected to the movable apparatus part when the first fasteners are connected with the corresponding second fasteners; and an electrical monitoring unit configured to electrically monitor an electrical resistance of the releasable connection of the plurality of first fasteners to the second fasteners.

2. An arrangement of a medical imaging device with a movable apparatus part, the arrangement comprising:

a mat-like, removable collision detection device arranged on a housing of the movable apparatus part of the medical imaging device;

a plurality of first fasteners arranged on the removable collision detection device, the plurality of first fasteners being configured to form a releasable connection with corresponding second fasteners, the second fasteners being arranged on the housing, the collision detection device being connected to the housing when the first fasteners are connected with the corresponding second fasteners; and a monitoring unit configured to electrically monitor an electrical resistance of the connection of the plurality of first fasteners to the second fasteners.

3. The arrangement of claim 1, wherein the plurality of first fasteners and the second fasteners are electrically conductive.

4. The arrangement of claim 2, wherein the plurality of first fasteners and the second fasteners are electrically conductive.

5. The arrangement of claim 1, wherein the plurality of first fasteners and the second fasteners are configured as press studs or hook-and-loop fasteners.

6. The arrangement of claim 2, wherein the plurality of first fasteners and the second fasteners are configured as press studs or hook-and-loop fasteners.

7. The arrangement of claim 1, further comprising:

an output unit configured to optically, acoustically, or optically and acoustically indicate the state of the connections between corresponding first fasteners and second fasteners.

8. The arrangement of claim 2, further comprising:

an output unit configured to optically, acoustically, or optically and acoustically indicate the state of the connections between corresponding first fasteners and second fasteners.

9. The arrangement of claim 7, wherein the output unit is configured to emit a warning signal, to stop a movement of the moveable apparatus part, or a combination thereof when the electrical monitoring unit detects an open connection between one of the corresponding first and second fasteners.

10. The arrangement of claim 8, wherein the output unit is configured to emit a warning signal, to stop a movement of the moveable apparatus part, or a combination thereof when the monitoring unit detects an open connection between one of the corresponding first and second fasteners.

11. The arrangement of claim 3, wherein the electrical monitoring unit is configured to determine an electrical resistance between adjacent second fasteners, and wherein adjacent corresponding first fasteners are electrically short-circuited to each other.

12. The arrangement of claim 4, wherein the monitoring unit is configured to determine an electrical resistance between adjacent second fasteners, and wherein adjacent corresponding first fasteners are electrically short-circuited to each other.

13. A medical imaging apparatus comprising:

an arrangement with a movable apparatus part, the arrangement comprising:

a mat-like, removable collision detection device arranged on the movable apparatus part;

a plurality of first fasteners arranged on the collision detection device, the plurality of first fasteners being configured to form a releasable connection with corresponding second fasteners, the second fasteners being arranged on the movable apparatus part, the collision detection device being connected to the movable apparatus part when the first fasteners are connected with the corresponding second fasteners; and an electrical monitoring unit configured to electrically monitor an electrical resistance of the releasable connection of the plurality of first fasteners to the second fasteners.

14. A method for operating a mat-like collision detection device arranged removably on a moved apparatus part of a medical imaging device, the method comprising:

electrically monitoring an electrical resistance of a connection of first fasteners arranged on the collision detection device to corresponding second fasteners arranged on the moved apparatus part.

15. The method of claim 14, further comprising determining the electrical resistance between adjacent second fasteners, wherein the first fasteners and the second fasteners are electrically conductive, and corresponding adjacent first fasteners are short-circuited.

16. A method for operating a mat-like collision detection device arranged removably on a housing of a moved apparatus part of a medical imaging device, the method comprising:

electrically monitoring an electrical resistance of a connection of first fasteners arranged on the collision detection device to corresponding second fasteners arranged on the housing.

17. The method of claim 16, further comprising determining the electrical resistance between adjacent second fasteners, wherein the first fasteners and the second fasteners are electrically conductive, and corresponding adjacent first fasteners are short-circuited.

\* \* \* \* \*